United States Patent [19]

Sawada et al.

[11] Patent Number: 6,166,189
[45] Date of Patent: Dec. 26, 2000

[54] PROCESS FOR PRODUCTION OF ALKYL GLYCOSIDE STABLE IN HUE AND ODOR

[75] Inventors: Hiroki Sawada; Hiroshi Nagumo; Toyomi Koike; Akio Kimura; Akira Yamamuro, all of Wakayama, Japan

[73] Assignee: Kao Corporation, Tokyo, Japan

[21] Appl. No.: 07/867,089

[22] Filed: Apr. 14, 1992

Related U.S. Application Data

[63] Continuation of application No. 07/494,367, Mar. 16, 1990, abandoned.

[30] Foreign Application Priority Data

Mar. 17, 1989 [JP] Japan ..................................... 1-65390
Mar. 31, 1989 [JP] Japan ..................................... 1-80275

[51] Int. Cl.$^7$ .............................. C07H 15/00; C07H 1/00; C07H 1/06
[52] U.S. Cl. ...................... 536/18.6; 536/18.5; 536/124; 536/127
[58] Field of Search ................................. 536/18.6, 18.5, 536/127, 124

[56] References Cited

U.S. PATENT DOCUMENTS

| | | | |
|---|---|---|---|
| 3,100,732 | 8/1963 | Smedberg | 162/78 |
| 3,565,885 | 2/1971 | Molotsky et al. | 536/18.6 |
| 4,483,979 | 11/1984 | Mao | 536/18.6 |
| 4,557,729 | 12/1985 | McDaniel et al. | 536/18.5 |
| 4,762,918 | 8/1988 | McDaniel et al. | 536/127 |
| 4,800,038 | 1/1989 | Broze et al. | 536/18.6 |
| 4,904,774 | 2/1990 | McDaniel et al. | 536/127 |
| 4,950,743 | 8/1990 | McCurry et al. | 536/18.5 |
| 4,959,468 | 9/1990 | Ravi et al. | 536/127 |

FOREIGN PATENT DOCUMENTS 0165721   12/1985   European Pat. Off. .

OTHER PUBLICATIONS

Derwent Abstract of Japanese Patent Application No. 58–189195.
Derwent Abstract of Japanese Patent Application No. 59–139397.
Derwent Abstract of Japanese Patent Application No. 60–1196.
Derwent Abstract of Japanese Patent Application No. 62–192396.

*Primary Examiner*—Gary Geist
*Assistant Examiner*—Everett White
*Attorney, Agent, or Firm*—Sughrue, Mion, Zinn, Macpeak & Seas, PLLC

[57] ABSTRACT

A process is disclosed for the production of an alkyl glycoside stable in hue and odor, which comprises the steps of (1) reacting a sugar with alcohol to obtain an alkyl glycoside reaction product containing a higher alcohol, (2) decoloring the alkyl glycoside reaction product with hydrogen peroxide, (3) contacting the decolored alkyl glycoside with a metal/hydrogen complex represented by formula (I)

$$M(BH_4)_z \qquad (I)$$

wherein M is an alkali metal, Ca, Zn or $(CH_3)_4N$; and
z is 1 when M is an alkali metal or $(CH_3)_4N$ and z is 2 when M is Ca or Zn; to substantially eliminate residual hydrogen peroxide, and then (4) decomposing the remaining metal/hydrogen complex with an acid.

11 Claims, No Drawings

PROCESS FOR PRODUCTION OF ALKYL GLYCOSIDE STABLE IN HUE AND ODOR

This is a Continuation of application Ser. No. 07/494,367 filed Mar. 16, 1990 abandoned.

FIELD OF THE INVENTION

This invention relates to a process for the production of an alkyl glycoside. More particularly, it relates to a process for the production of an alkyl glycoside which is excellent in hue, odor, and stability.

BACKGROUND OF THE INVENTION

An alkyl glycoside is a sugar derivative surfactant which is less irritating than other surfactant. Also, though it is a nonionic surfactant, alkyl glycosides form a stable foam per se, and furthermore, exert a foam-stabilizing effect on other anionic surfactants. These characteristics make alkyl glycosides highly noteworthy.

Although alkyl glycosides as novel surfactants have the above-mentioned noteworthy characteristics, it is quite difficult to produce them in the form of a commercially useful product. A most serious problem in the production of alkyl glycosides is that various procedures during the production process thereof frequently cause deterioration of the hue of the product. Furthermore, the alkyl glycoside thus produced suffers from deterioration of hue upon storage with the lapse of time.

In order to produce an alkyl glycoside which has a good hue sufficient to be useful for application in a commercial product, it has been found necessary to decolor alkyl glycoside that has been obtained by reacting a sugar with an alcohol. However, the use of hydrogen peroxide (which is commonly known as an effective decoloring agent) in the decoloring of the alkyl glycoside is accompanied by other new problems, such as, for example, deterioration with respect to odor, caused by rancidity and aldehyde smells evolving upon storage, and deterioration in the hue with the lapse of time.

Accordingly, there have been attempts to improve the hue of an alkyl glycoside. For example, JP-A-59-65098 (the term "JP-A" as used herein means an "unexamined published Japanese patent application") (corresponding to U.S. Pat. No. 4,704,453) discloses a process wherein a reducing sugar is acetalized in the presence of an alkali borate in an amount equivalent to, or exceeding, an acid catalyst; JP-A-59-139397 discloses a process wherein acetalization is conducted in the presence of an acid catalyst and a reducing agent; and JP-A-60-1196 discloses a process wherein acetalization is conducted with the use of a perfluorosulfonic acid resin as a catalyst. Furthermore, European Patent 0132046 reports a process wherein a catalyst is neutralized with an organic base after the completion of an acetalization reaction; JP-A-58-194902 (corresponding to U.S. Pat. No. 3,565,885) discloses a process wherein a residual alcohol is removed by using a thin film evaporator; U.S. Pat. No. 3,450,690 discloses a process wherein alkali labile color-producing bodies are removed by treating with an alkali; and JP-A-47-16413 (corresponding to U.S. Pat. No. 3,565,885) discloses a process wherein said removal is conducted with the use of a hydroxyl type anion exchange resin. Furthermore, JP-A-62-192396 discloses a process wherein a viscosity depressant is added upon the separation of the formed alkyl glycoside from the unreacted and recovered alcohol, since the high viscosity and poor heat stability of the alkyl glycoside causes particularly serious deterioration of the hue.

In addition, JP-A-1-290692 discloses a process for improving the color of a glycoside composition which comprises contacting a glycoside composition containing colored human with a hydrogen source (for example, hydrogen or sodium borohydride), but the product is still deficient in hue (see Comparative Example 4 below).

However, none of the foregoing methods can provide an alkyl glycoside which shows a satisfactory hue when applied to a commercial product in practice.

JP-A-61-33193 (corresponding to U.S. Pat. No. 4,557,729) discloses bleaching the finally obtained alkyl glycoside with hydrogen peroxide and sulfur dioxide. In this case, however, the odor of the alkyl glycoside immediately after the treatment is inferior to that prior to the treatment. Furthermore, the alkyl glycoside thus obtained suffers from deterioration in the hue and odor with the lapse of time upon storage. Thus, this is not an effective measure.

As described above, it is important that the hue and odor of an alkyl glycoside which has been decolored with hydrogen peroxide be stable upon storage. Since this problem has never been overcome so far, it has been urgently required to establish a solution thereto.

SUMMARY OF THE INVENTION

Under these circumstances, we have conducted extensive studies in order to solve the foregoing problems which occur upon the decoloring of an alkyl glycoside. As a result, we have found that deterioration of the hue and odor observed in the storage of an alkyl glycoside which has been decolored with hydrogen peroxide is caused by the hydrogen peroxide remaining in the alkyl glycoside after the completion of the decoloring. We have further found that the residual hydrogen peroxide can be efficiently decomposed by contacting with a specific metal/hydrogen complex, and that the treatment results in a highly stable hue and a highly stable odor of the alkyl glycoside upon storage, thus completing the present invention.

Accordingly, the present invention provides a process for the production of an alkyl glycoside stable in hue and odor, which comprises the steps of (1) reacting a sugar with an alcohol, to obtain an alkyl glycoside reaction product containing a higher alcohol, (2) decoloring the alkyl glycoside reaction product thus obtained with hydrogen peroxide, (3) contacting the decolored alkyl glycoside with a metal/hydrogen complex represented by formula (I)

$$M(BH4)_z \qquad (I)$$

wherein M is an alkali metal, Ca, Zn or $(CH_3)_4N$; and z is 1 when M is an alkali metal or $(CH_3)_4N$ and z is 2 when M is Ca or Zn; to substantially eliminate residual hydrogen peroxide, and then, (4) decomposing the remaining metal/hydrogen complex with an acid.

As described above, it is an object of the present invention to obtain an alkyl glycoside excellent in hue and odor by efficiently decomposing the hydrogen peroxide remaining in the alkyl glycoside by contacting with a specific metal/hydrogen complex, different from the process described in JP-A-1-290692 wherein an alkyl glycoside composition containing, for example, color bodies is reduced and decolored with hydrogen or a hydrogen source.

DETAILED DESCRIPTION OF THE INVENTION

The alkyl glycoside reaction product of the present invention is obtained by a commonly known method. For example, it may be obtained either by directly reacting a sugar with a higher alcohol in the presence of an acid catalyst, or by preliminarily reacting a sugar with a lower alcohol (for example, methanol, ethanol, propanol, butanol) to thereby provide a lower alkyl glycoside, which is then reacted with a higher alcohol.

The higher alcohol for use in the process of the present invention is represented by formula (II)

$$R_1O(R_2O)_xH \qquad (II)$$

wherein $R_1$ represents a straight or branched alkyl, alkenyl, or alkylphenyl group having from 6 to 22 carbon atoms;

$R_2$ represents an alkylene group having from 2 to 4 carbon atoms; and x indicates a mean value and is a number equal to 0 to 5.

Specific examples of the higher alcohol represented by formula (II) include a straight or branched alkanol such as hexanol, heptanol, octanol, nonanol, decanol, dodecanol, tridecanol, tetradecanol, pentadecanol, hexadecanol, heptadecanol, octadecanol, methylpentanol, methylhexanol, methylheptanol, methyloctanol, methyldecanol, methylundecanol, methyltridecanol, methylheptadecanol, ethylhexanol, ethyloctanol, ethyldecanol, ethyldodecanol, 2-heptanol, 2-nonanol, 2-undecanol, 2-tridecanol, 2-pentadecanol, 2-heptadecanol, 2-butyloctanol, 2-hexyloctanol, 2-octyloctanol, 2-hexyldecanol and 2-octyldecanol; an alkenol such as hexenol, heptenol, octenol, nonenol, decenol, undecenol, dodecenol, tridecenol, tetradecenol, pentadecenol, hexadecenol, heptadecenol and octadecenol; and alkylphenols such as octylphenol and nonylphenol. These alcohols or alkylphenols may be used either alone or a mixture of two or more of them. Further, an alkylene oxide adduct of these alcohols or alkylphenols can be used.

The sugar for use as the starting material for the production of the alkyl glycoside according to the present invention may be selected from monosaccharides, oligosaccharides, and polysaccharides. Examples of the monosaccharides include aldoses such as allose, altrose, glucose, mannose, gulose, idose, galactose, talose, ribose, arabinose, xylose, lyxose. Examples of the oligosaccharides include maltose, lactose, sucrose and maltotriose. Examples of the polysaccharides include hemicellulose, insulin, dextrin, dextran, xylan, starch and hydrolyzed starch.

In the present invention, the production of an alkyl glycoside may be conducted with the use of the above-mentioned starting materials under known conditions (for example, catalyst, temperature) as disclosed, for example, in JP-B-47-24532 (the term "JP-B" as used herein means an "examined Japanese patent publication") (corresponding to U.S. Pat. No. 3,598,865), U.S. Pat. No. 3,839,318, European Patent 092355, JP-A-59-139397, and JP-A-58-189195.

As the alkyl glycoside to be decolored according to the process of the present invention, those represented by formula (III) are particularly preferable:

$$R_1O(R_2O)_xG_y \qquad (III)$$

wherein $R_1$ is an alkyl, alkenyl, or alkylphenyl group having from 6 to 22 carbon atoms;

$R_2$ is an alkylene group having from 2 to 4 carbon atoms;

G is a residual group originating from a reducing sugar having 5 or 6 carbon atoms;

x indicates a mean value and is a number equal to 0 to 5; and y indicates a mean value and is a number equal to 1 to 10.

In the present invention, the decoloring of the alkyl glycoside with hydrogen peroxide can be efficiently conducted in a system wherein the pH value is maintained within an alkaline region. The amount of the hydrogen peroxide to be used in the decoloring may range from 0.05 to 10% by weight, based on the dry solid alkyl glycoside content, and preferably from 0.1 to 5% by weight. The alkyl glycoside to be decolored is used in the form of an aqueous solution of the alkyl glycoside containing 15 to 75% by weight, and preferably 35 to 65% by weight, based on the dry solid alkyl glycoside content. In the process of the present invention, it is preferable to and still more preferably from about 8.5 to 12, from the viewpoints of the color and odor of the alkyl glycoside.

The treatment with hydrogen peroxide is accompanied by a decrease in the pH value of the alkyl glycoside aqueous solution. Therefore an alkali may be optionally added to the system throughout the treatment to thereby maintain the pH value of the system at about 8.5 or above. Examples of the alkali to be used for maintaining the pH value at the desired level include alkali metal hydroxides (for example, sodium hydroxide, potassium hydroxide) or alkali metal carbonates (for example, sodium carbonate, potassium carbonate) and each may be used in the form of either a solid or an aqueous solution.

The treatment with hydrogen peroxide in the process of the present invention may be effected by adding a required amount of hydrogen peroxide to the alkyl glycoside aqueous solution followed by stirring or aging for 30 minutes or longer, preferably for one hour or longer. The hydrogen peroxide is usually added in the form of a 3 to 60% by weight aqueous solution, though the present invention is not restricted thereto. The hydrogen peroxide may be added either at once or by portions. This treatment may generally be conducted at from 5 to 100° C., preferably at from 20 to 80° C., and still more preferably at from 30 to 70° C.

Examples of the metal/hydrogen complex of the formula (I) to be used in the present invention include lithium borohydride, sodium borohydride, potassium borohydride, tetramethylammonium borohydride, calcium borohydride and zinc borohydride. Among these substances, sodium borohydride is particularly preferable.

The metal/hydrogen complex of the formula (I) to be used in the present invention may be added to the alkyl glycoside aqueous solution, which has been decolored with hydrogen peroxide, either as such (i.e., in the form of a powder) or in the form of an aqueous solution or an alkaline aqueous solution. The amount of the metal/hydrogen complex to be added generally ranges from 0.05 to 2 mole equivalents, and preferably from 0.3 to 1 mole equivalent, with respect to the hydrogen peroxide used for the decoloring. This treatment is generally conducted at from 10 to 80° C., and preferably at from 20 to 50° C. This treatment is generally conducted for from 0.25 to 5 hours, and preferably for from 0.5 to 1 hour, at a pH value of from about 7 to 12, and preferably from about 8 to 10. The pH value may be adjusted to the desired level by adding an appropriate base (for example, sodium hydroxide) prior to the addition of the metal/hydrogen complex.

Next, the excess metal/hydrogen complex remaining in the system is decomposed with an acid, to thereby complete the treatment. Examples of the acid include sulfuric acid and p-toluenesulfonic acid. An acid is slowly added while stirring to the alkyl glycoside aqueous solution containing the excess metal/hydrogen complex so as to maintain the pH value of the system weakly acidic. The decomposition of the metal/hydrogen complex requires approximately 0.5 hour.

After the completion of the decomposition, the pH value is adjusted to neutral by adding an appropriate base, for example, sodium hydroxide.

Thus, the hydrogen peroxide remaining in the alkyl glycoside aqueous solution can be completely decomposed and eliminated. The amount of the hydrogen peroxide remaining in the system can be readily determined by, for example, iodometric titration (Eisei Shiken Chu-kai, editted by Pharmaceutical Society of Japan, p. 192 (1973)).

The present invention is characterized by treating an alkyl glycoside aqueous solution, which has been decolored with hydrogen peroxide, with a metal/hydrogen complex of the formula (I). This treatment brings about a surprising effect of maintaining the hue and odor of the obtained alkyl glycoside excellent for a prolonged period of time.

To further illustrate the present invention, and not by way of limitation, the following Examples are described. Unless otherwise indicated, all percents are by weight.

EXAMPLE 1

(a) 1140 g (72.0 mol) of decyl alcohol, 3240 g (18.0 mol) of anhydrous glucose and 96 g (0.5 mol) of p-toluene-sulfonic acid monohydrate were heated and stirred in a 30 liter reaction vessel. After heating to 95° C., the pressure in the reaction system was adjusted to 40 mmHg, and then dehydration was initiated. Then $N_2$ was blown into the reaction mixture at a rate of 0.3 $Nm^3/h$ so as to efficiently remove the water formed during the reaction. After five hours, it was confirmed that the reaction mixture had turned transparency, namely the solid glucose had been completely consumed. Next, the reduced pressure was relieved and the reaction mixture was cooled and neutralized with 20 g of NaOH. After filtering the polysaccharides formed as by-products, 4270 g of the alkyl glycoside was separated from 8460 g of the unreacted alcohol by distillation at 130° C. under 0.4 mmHg. Next, some portion of the solid matters was dissolved in water to thereby prepare a 50% aqueous solution of a dark red color. (Hue: Gardner 8)

(b) 400 g of this aqueous solution of the alkyl glycoside was heated to 45° C. and 10 g of a 3% aqueous solution of NaOH was added thereto to thereby adjust the pH value to 9. Then 4 g of a 30% aqueous solution of hydrogen peroxide ($H_2O_2$) was added thereto and the mixture was stirred at 45° C. for 30 minutes. During this period, the pH value was maintained at 8.7 to 9.3 by appropriately adding a 3% aqueous solution of NaOH.

Next, 0.67 g of sodium borohydride was added thereto, and the mixture was stirred for 30 minutes at room temperature. Then the pH value was adjusted to 5 by adding a 5% aqueous solution of p-toluenesulfonic acid. After stirring for 30 minutes, the pH value was adjusted to 7 by adding a 3% aqueous solution of NaOH. The amount of the $H_2O_2$ remaining in the alkyl glycoside aqueous solution was so small that it could not be determined by iodometric titration.

EXAMPLE 2

The procedure of Example 1 was repeated except that the sodium borohydride was replaced by 1.2 g of calcium borohydride, to thereby provide an alkyl glycoside aqueous solution.

COMPARATIVE EXAMPLE 1

The procedure of Example 1 was repeated except that no sodium borohydride treatment was conducted, to thereby provide an aqueous solution.

In this case, 0.14% by weight of $H_2O_2$ remained.

COMPARATIVE EXAMPLE 2

400 g of the aqueous solution of alkyl glycoside prepared in Example 1(a) was heated to 45° C. and 10 g of 3% aqueous solution of NaOH was added thereto to adjust the pH value to 9. Then, 4 g of 30% aqueous solution of hydrogen peroxide was added thereto and the resulting mixture was stirred at 45° C. During this period, the pH value of the reaction mixture was not adjusted further, and the pH values after 10 minutes and 30 minutes were 7.8 and 7.7, respectively.

Next, 0.67 g of sodium borohydride was added thereto and the mixture was stirred at room temperature for 30 minutes.

After stirring, the pH value of the mixture was adjusted to 5 by adding a 5% aqueous solution of p-toluenesulfonic acid. After stirring for 30 minutes, the pH value of the mixture was adjusted to 7 by adding a 3% aqueous solution of NaOH. The amount of the hydrogen peroxide remaining in the alkyl glycoside aqueous solution was so small that it could not be determined by iodometric titration.

COMPARATIVE EXAMPLE 3

The procedure of Example 1 was repeated except that the sodium borohydride was replaced by 0.38 g of sodium sulfite, to thereby provide an alkyl glycoside aqueous solution.

COMPARATIVE EXAMPLE 4

An alkyl glycoside was decolored according to the process of JP-A-1-290692.

Namely, a 50% aqueous solution of an alkyl glycoside of a dark red color was prepared by the same method as described in Example 1-(a).

200 g of the alkyl glycoside aqueous solution thus obtained was completely mixed with 4.2 g of a 14 N NaOH solution containing 12% by weight of sodium borohydride. The mixture obtained was then allowed to stand at room temperature for 4 days.

TEST EXAMPLE 1

Each of the alkyl glycoside aqueous solutions obtained Examples 1 and 2 and Comparative Examples 1 to 4 was used to an alkyl glycoside content of 30% by weight. Then storage stability of each product was evaluated in air at 50° C. for 120 hours. Table 1 summarizes the results.

In Table 1, a lower Gardner value shows the better hue. Each odor was evaluated by five panelists, and the one of which most of the panelists have detected are indicated in the table.

TABLE 1

| Example No. | Chemical Treatment for Aqueous Solution of Alkylglycoside | | | Quality Evaluation of Aqueous Solution of Alkylglycoside | | | | |
|---|---|---|---|---|---|---|---|---|
| | Condition at $H_2O_2$ Treatment | | Metal/hydrogen Complex (% by wt.) | At the initiation | | | After 120 hours | |
| | pH | Temperature (° C.) | | Remaining $H_2O_2$ (Gardner) | Hue | Odor (Gardner) | Hue | Odor |
| Example 1 | 8.7 to 9 | 45 | sodium borohydride | undetectable | 1 | no | 1 | no |
| Example 2 | 8.7 to 9 | 45 | calcium borohydride | undetectable | 1 | no | 1 | no |
| Comparative Example 1 | 8.7 to 9 | 45 | not used | 0.14 | 1 | no | 3 | aldehyde-like |
| Comparative Example 2 | 9 to 7 | 45 | sodium borohydride | undetectable | 7 | no | 7 | no |
| Comparative Example 3 | 8.7 to 9 | 45 | sodium sulfite | undetectable | 1 | no | 6 | sulfur-like |
| Comparative Example 4 | not treated | | sodium borohydride | 0.00 | 8 | no | 8 | alkali-like |

Table 1 indicates that an alkyl glycoside having excellently stabilized hue and odor can be obtained by the process of the present invention.

EXAMPLE 3

28260 g of one mole ethylene oxide adduct of Diadol 18G (manufactured by Mitsubishi Kasei Corporation) (90 mol), 3240 g of anhydrous galactose (18 mol) and 96 g of p-toluenesulfonic acid monohydrate (0.5 mol) were heated to 95° C. and stirred under 40 mmHg, and dehydration was initiated, while blowing in nitrogen gas at a rate of 0.3 Nm³/h so as to efficiently distill off the water thus formed. After confirming that the reaction mixture had turned transparency, namely the solid galactose had been completely consumed, the reduced pressure was relieved and the reaction mixture was cooled and neutralized with 20 g of NaOH. After filtering the polysaccharides formed as by-products, 7880 g of alkyl galactoside was separated from 23600 g of the unreacted alcohol by distillation at 200° C. under the pressure of 0.3 mmHg. Next, some portion of the solid matters was dissolved in water to thereby prepare a 50% aqueous solution of a dark red color. (Hue: Gardner 10)

The thus obtained solution was decolored by hydrogen peroxide in the same manner as in Example 1(b) and then treated with sodium borohydride.

COMPARATIVE EXAMPLE 5

An alkyl glycoside solution was obtained in the same manner in Example 3, except that sodium borohydride was not used.

The amount of hydrogen peroxide remaining in the alkyl glycoside solution was 0.15% by weight.

COMPARATIVE EXAMPLE 6

The procedure of Example 3 was repeated to prepare an alkyl glycoside aqueous solution, except that the pH value, which had been adjusted to 9.0 at the initiation of the treatment, was not adjusted further. The pH value after 10 minutes and 30 minutes were 7.6 and 7.5, respectively.

TEST EXAMPLE 2

Each of the alkyl glycoside aqueous solutions obtained in Example 3 and Comparative Examples 5 and 6 was adjusted to an alkyl glycoside content of 30% by weight. Then, the storage stability of each product was evaluated in air at 50° C. for 120 hours. Table 2 summarizes the results.

TABLE 2

| | At the initiation | | | After 120 hours | |
|---|---|---|---|---|---|
| Example No. | Remaining $H_2O_2$ (% by wt.) | Hue (Gardner) | Odor | Hue (Gardner) | Odor |
| Example 3 | undetectable | 2 | no | 2 | no |
| Comparative Example 5 | 0.15 | 2 | no | 4 | aldehyde-like |
| Comparative Example 6 | undetectable | 7 | no | 7 | no |

Table 2 indicates that an alkyl glycoside having excellently stabilized hue and odor can be obtained by the process of the present invention.

While the invention has been described in detail and with reference to specific examples thereof, it will be apparent to one skilled in the art that various changes and modifications can be made therein without departing from the spirit and scope thereof.

What is claimed is:

1. A process for the production of an alkyl glycoside stable in hue and odor, which comprises the steps of (1) reacting a sugar with alcohol to obtain an alkyl glycoside reaction product containing a higher alcohol, (2) decoloring the alkyl glycoside reaction product with hydrogen peroxide, (3) contacting the decolored alkyl glycoside with a metal/hydrogen complex represented by formula (I)

$$M(BH_4)_z \qquad (I)$$

wherein M is an alkali metal, Ca, Zn or $(CH_3)_4N$; and z is 1 when M is an alkali metal or $(CH_3)_4N$ and z is 2 when M is Ca or Zn; to substantially eliminate residual hydrogen peroxide, and then (4) decomposing the remaining metal/hydrogen complex with an acid.

2. A process for the production of an alkyl glycoside as in claim 1, wherein the alkyl glycoside reaction product is obtained by reacting said sugar with a higher alcohol.

3. A process for the production of an alkyl glycoside as in claim 1, wherein the alkyl glycoside reaction product is obtained by first reacting said sugar with a lower alcohol, and then reacting the product obtained with the higher alcohol.

4. A process for the production of an alkyl glycoside as in claim 1, wherein said metal/hydrogen complex represented by formula (I) is sodium borohydride.

5. A process for the production of an alkyl glycoside as in claim 1, wherein the acid is at least one selected from the group consisting of sulfuric acid and p-toluenesulfonic acid.

6. A process for the production of an alkyl glycoside as in claim 1, wherein the decoloring with hydrogen peroxide is conducted while maintaining the pH value of the aqeuous solution of alkyl glycoside reaction product at about 8.5 or above.

7. A process for the production of an alkyl glycoside as in claim 1, wherein said alkyl glycoside is a compound represented by formula (III)

$$R_1O(R_2O)_xG_y \qquad (III)$$

wherein $R_1$ is an alkyl, alkenyl, or alkylphenyl group having 6 to 22 carbon atoms;

$R_2$ is an alkylene group having 2 to 4 carbon atoms;

G is a residual group originating from a reducing sugar having 5 or 6 carbon atoms;

x indicates a mean value and is a number equal to 0 to 5; and y indicates a mean value and is a number equal to 1 to 10.

8. A process for the production of an alkyl glycoside as in claim 7, wherein said metal/hydrogen complex is sodium borohydride.

9. A process for the production of an alkyl glycoside as in claim 1, wherein the amount of the metal/hydrogen complex is from 0.05 to 2 mol equivalents with respect of the hydrogen peroxide used for the decoloring, and step (3) is conducted at a temperature of from 10 to 80° C. for from 0.25 to 5 hours at a pH value of from about 7 to 12.

10. A process for the production of an alkyl glycoside as in claim 1, wherein the amount of the metal/hydrogen complex is from 0.3 to 1 mol equivalent with respect to the hydrogen peroxide used for the decoloring, and step (3) is conducted at a temperature of from 20 to 50° C. for from 0.5 to 1 hour at a pH value of from about 8 to 10.

11. A process for the production of an alkyl glycoside as in claim 8, wherein said metal/hydrogen complex is sodium borohydride.

* * * * *